(12) United States Patent
Webber et al.

(10) Patent No.: US 10,973,612 B2
(45) Date of Patent: Apr. 13, 2021

(54) DENTAL APPLIANCE BINDING STRUCTURE

(71) Applicant: Align Technology, Inc., San Jose, CA (US)

(72) Inventors: Peter Webber, Redwood City, CA (US); Jennifer C. Chen, San Francisco, CA (US); Yan Chen, Cupertino, CA (US); Bastien Pesenti, Santa Clara, CA (US); Crystal Tjhia, Sunnyvale, CA (US)

(73) Assignee: Align Technology, Inc., San Jose, CA (US)

( * ) Notice: Subject to any disclaimer, the term of this patent is extended or adjusted under 35 U.S.C. 154(b) by 170 days.

(21) Appl. No.: 16/202,369

(22) Filed: Nov. 28, 2018

(65) Prior Publication Data

US 2019/0090983 A1  Mar. 28, 2019

Related U.S. Application Data

(62) Division of application No. 14/734,774, filed on Jun. 9, 2015, now Pat. No. 10,213,277.

(51) Int. Cl.
*A61C 7/00* (2006.01)
*A61C 7/36* (2006.01)
(Continued)

(52) U.S. Cl.
CPC .............. *A61C 7/002* (2013.01); *A61C 7/08* (2013.01); *A61C 7/36* (2013.01); *A61C 13/0004* (2013.01); *G16H 50/50* (2018.01)

(58) Field of Classification Search
CPC .............. A61C 7/08; A61C 7/002; A61C 7/36
See application file for complete search history.

(56) References Cited

U.S. PATENT DOCUMENTS 5,794,627 A   8/1998  Frantz et al.
6,604,527 B1  8/2003  Palmisano
(Continued)

FOREIGN PATENT DOCUMENTS

WO    2013102095      7/2013
WO    2016042393 A1   3/2016
WO    WO2016/198934 A1  12/2016

OTHER PUBLICATIONS

International Search Report from PCT Application PCT/IB2016/000729, dated Dec. 15, 2016, 6 pp.

*Primary Examiner* — Eric D. Bertram
(74) *Attorney, Agent, or Firm* — Shay Glenn LLP

(57) ABSTRACT

The present disclosure provides methods, computing device readable medium, devices, and systems having a dental appliance binding structure. One method can include to create a treatment plan based on a virtual model of a jaw of a patient, wherein the treatment plan includes use of a dental appliance having a first surface that defines a plurality of cavities shaped to receive a plurality of teeth, modify the virtual model of the jaw in a first configuration to include a virtual binding structure on a second surface, the platform shaped to receive a specialized feature that provides one or more force characteristics, select a particular specialized feature as an attachment to the dental appliance, and adjust the virtual model of the jaw from a first configuration to a second configuration, based at least in part on a modeled force provided by the virtual binding structure and the particular specialized feature.

25 Claims, 8 Drawing Sheets

(51) Int. Cl.
*G16H 50/50* (2018.01)
*A61C 13/00* (2006.01)
*A61C 7/08* (2006.01)

(56) References Cited

U.S. PATENT DOCUMENTS

| | | | |
|---|---|---|---|
| 8,001,973 B2 | 8/2011 | Sotos et al. | |
| 8,025,063 B2 | 9/2011 | Sotos et al. | |
| 8,037,886 B2 | 10/2011 | Sotos et al. | |
| 9,844,424 B2 * | 12/2017 | Wu | A61C 7/36 |
| 10,213,277 B2 | 2/2019 | Webber et al. | |
| 10,537,406 B2 * | 1/2020 | Wu | A61C 7/08 |
| 2003/0190575 A1 | 10/2003 | Hilliard | |
| 2003/0207224 A1 * | 11/2003 | Lotte | A61C 7/36 433/6 |
| 2003/0224313 A1 | 12/2003 | Bergersen | |
| 2004/0009449 A1 | 1/2004 | Mah et al. | |
| 2006/0078840 A1 | 4/2006 | Robson | |
| 2010/0138025 A1 * | 6/2010 | Morton | G06F 17/10 700/104 |
| 2011/0269092 A1 | 11/2011 | Kuo et al. | |
| 2013/0089828 A1 | 4/2013 | Borovinskih | |
| 2013/0095446 A1 | 4/2013 | Andreiko | |
| 2015/0079531 A1 | 3/2015 | Heine | |

\* cited by examiner

DENTAL APPLIANCE BINDING STRUCTURE

PRIORITY INFORMATION

This application is a Divisional of U.S. application Ser. No. 14/734,774, filed Jun. 9, 2015, now U.S. Pat. No. 10,213,277, the entire contents of which are hereby incorporated by reference.

BACKGROUND

The present disclosure provides methods, computing device readable medium, devices, and systems that utilize a dental appliance binding structure during dental treatment. Dental treatments involve restorative and/or orthodontic procedures to improve the quality of life of a patient.

For example, restorative procedures may be designed to implant a dental prosthesis (e.g., a crown, bridge, inlay, onlay, veneer, etc.) intraorally in a patient. Orthodontic procedures may include repositioning misaligned teeth and changing bite configurations for improved cosmetic appearance and/or dental function. Orthodontic repositioning can be accomplished, for example, by applying controlled forces to one or more teeth or a jaw of a patient over a period of time.

As an example, orthodontic repositioning may be provided through a dental process that uses positioning appliances for realigning teeth. Such appliances may utilize a shell of material having resilient properties, referred to as an "aligner," that generally conforms to a patient's teeth but is slightly out of alignment with a current tooth configuration.

Placement of such an appliance over the teeth may provide controlled forces in specific locations to gradually move the teeth into a new configuration. Repetition of this process with successive appliances in progressive configurations can move the teeth through a series of intermediate arrangements to a final desired arrangement (e.g., a corrected jaw position).

Such systems typically utilize a set of appliances that can be used serially such that, as the teeth move, a new appliance from the set can be implemented to further move the teeth without having to take a new impression of the patient's teeth at every increment of tooth movement in order to make each successive appliance.

In various instances, teeth of a patient's upper jaw and teeth of the patient's lower jaw may contact in an incorrect or suboptimal manner (e.g., crowding, crossbite, deep bite). A proper fit of the occlusal surfaces of the teeth is necessary for proper biting and chewing, as well as desirable for aesthetic appearance. Otherwise, premature wear of the teeth, undesirable forces on the teeth, and/or undesirable forces on dental restorations may be experienced by the patient.

Appliances have been previously proposed to handle these issues but the design of the appliances to handle some issues cannot be created with the manufacturing processes being utilized presently or their manufacture is too complicated to be feasible using current manufacturing techniques.

With respect to jaw repositioning, previously proposed devices typically have not allowed for teeth to be repositioned while the jaw adjustment is ongoing. Further, such appliances are typically not comfortable or aesthetically pleasing.

DETAILED DESCRIPTION

The present disclosure provides methods, computing device readable medium, devices, and systems having a dental appliance binding structure. A device having such binding structures can be beneficial as it can allow the appliance to provide multiple functions in the treatment of a patient's issues and can shorten the time of treatment by concurrently providing multiple functions, in some instances.

Figure 1:
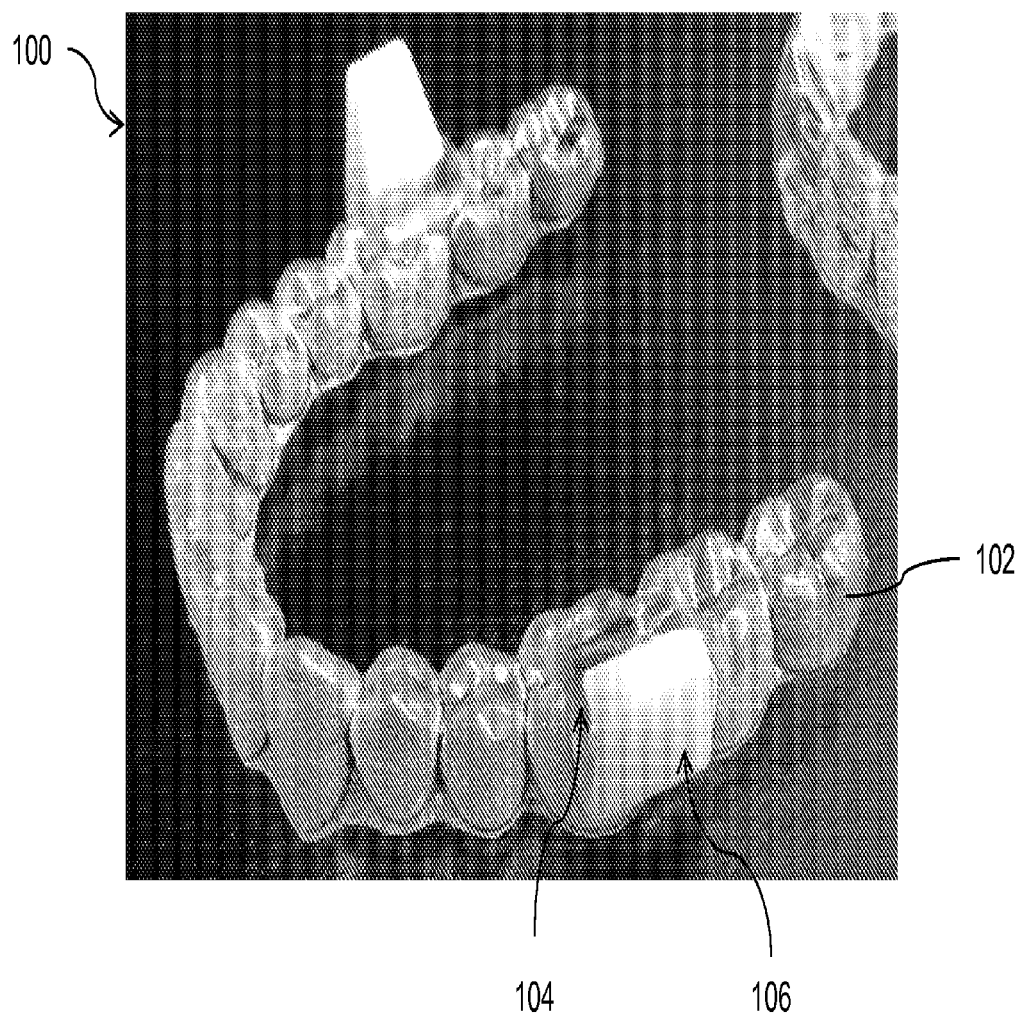
FIG. 1 illustrates an angled side view of a shell with two binding structures thereon with each structure having a specialized feature attached thereto according to a number of embodiments of the present disclosure.

FIG. 1 illustrates an angled side view of a shell with two binding structures thereon with each structure having a specialized feature attached thereto according to a number of embodiments of the present disclosure. FIG. 1 provides an example of an embodiment of a dental appliance 100 that has a shell 102 with a number of cavities for receiving teeth, a number of binding structures 104, and a number of specialized features 106 attached to the shell on at least one surface of the binding structure 104.

In the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and/or structural changes may be made without departing from the scope of the present disclosure.

As used herein, the designator "N", particularly with respect to reference numerals in the drawings, indicates that a number of the particular feature so designated can be included. As used herein, "a number of" a particular thing can refer to one or more of such things (e.g., a number of teeth can refer to one or more teeth).

The figures herein follow a numbering convention in which the first digit or digits correspond to the drawing figure number and the remaining digits identify an element or component in the drawing. Similar elements or components between different figures may be identified by the use of similar digits. For example, 106 may reference element "06" in FIG. 1, and a similar element may be referenced as 206 in FIG. 2.

As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate certain embodiments of the present disclosure, and should not be taken in a limiting sense.

In the example shown in FIG. 1, the binding structure includes a first binding surface (in this instance, a first attachment surface in the form of a planar platform on the outer occlusal surface of the appliance) and a second binding surface (a second attachment surface in the form of a planar side surface on the outer buccal surface of the appliance). In this manner, the specialized feature can be attached to one or more binding surfaces of the appliance. Attachment to multiple surfaces can be beneficial in some embodiments, for example, to increase the amount of force that can be applied by the feature and/or provide forces in multiple directions, among other benefits.

The method of attachment can be rigid or flexible, in some embodiments, and can have rigid and flexible portions along one binding surface, in various embodiments. For example, the attachment can be made via a rigid type adhesive in which the interposing attachment material between the binding surface and the specialized feature is rigid and thereby prohibits the movement of the specialized feature with respect to the binding surface.

Alternatively, a flexible type adhesive can be utilized in which the interposing attachment material between the binding surface and the specialized feature is flexible and thereby allows some movement of the specialized feature with respect to the binding surface. This can be beneficial in instances where some give or cushion is desirable.

When used in combination on different portions of the same surface, one benefit can be the application of forces by the specialized feature and/or shell in different degrees and in different directions than when one type of attachment material is utilized. This can allow for further customization of a treatment plan of a patient and/or additional uses for such specialized features, among other benefits.

As will be discussed in more detail below, in some embodiments, the attachment can be a mechanical form of attachment (e.g., lock and key type attachment, male and female locking attachment, etc.). Any suitable attachment structure can be utilized in embodiments of the present disclosure.

Additionally, in some embodiments, the attachment can be releasable, thereby allowing the specialized feature to be removable and, in some embodiments, replaceable with a same or different specialized feature. This can allow a patient or treatment professional to temporarily remove the specialized feature which allows the patient and the treatment professional flexibility in when the additional treatment the specialized feature provides is implemented.

Further, different types of specialized features can be utilized to provide different abilities to the appliance. Some embodiments can include multiple types of features on a single appliance and potentially multiple features on one binding surface, in some embodiments.

In various embodiments, a set of specialized features can be made available to a treatment professional. For example, a set of five specialized features can be provided and the treatment professional can select from those five features. In this manner, the treatment professional does not need to design their own feature, but rather can select the feature that will be most appropriate for the patient's issue.

This can allow the appliance to be specialized to the patient, but not be onerous on the treatment profession who, for example, may not have feature design capabilities. Such embodiments can also allow a treatment professional to see what types of conditions the appliance can potentially remedy based on the available specialized features provided in the set of features.

In some embodiments, the treatment professional may also select one or more attachment materials or attachment types and/or select the location upon which they should be applied. Such embodiments, can allow further customization of the appliance. Further, in various embodiments, this customization can be made for each appliance (or for multiple appliances) in a set of appliances of a treatment plan.

The following discussion relates to an example use for embodiments of the present disclosure related to use of one or more jaw repositioning elements as the attached specialized features to help the reader understand how an embodiment of the present disclosure may be utilized. However, the present disclosure should not be viewed as being limited to such specialized features. As the reader will understand, any suitable specialized feature that may resolve an issue in the patient's mouth can be mounted to a binding structure as described herein.

Generally, the repositioning of teeth occurs during an orthodontic treatment which is a process of moving and reorienting teeth for functional and/or aesthetic purposes, although repositioning may be made for other purposes. The repositioning of a jaw typically requires different mechanisms to do so than are used for tooth repositioning and, therefore, typically occurs at a different time during a treatment plan, thereby extending the treatment process.

Various embodiments of the present disclosure can accomplish both tooth adjustment and jaw adjustment at the same time through use of an aligner with one or more specialized features provided on one or more binding structures thereon. The appliance thereby has both capabilities and can shorten the time of treatment thereby improving the treatment process for the patient.

With respect to jaw movement, the maxilla (i.e., the upper jaw) is a bone that is fixed to the skull and the mandible (i.e., lower jaw) is a bone that is attached to the skull by numerous muscles which guide its movement and it is the interaction of these bones and muscles that provide a proper bite orientation for a patient. For instance, proper bite orientation can be a function of the relative positions of one or more teeth, the mandible, and/or the maxilla. For example, either of the mandible or maxilla may be retruded or protruded relative to an ideal position with respect to each other.

The mandible functions by articulating at its posterior upward extremities with the temporal bone to form the jaw joint. The jaw joint is a loosely connected joint that accommodates the variety of movements of the mandible relative to the maxilla during biting and chewing motions. The numerous muscles attaching the mandible to the skull control and power the complex movements involved in biting and chewing. Accordingly, it can be beneficial to the patient to have a properly aligned mandible.

Simultaneous contacting of the upper and lower teeth on the right and left sides, and in the anterior and posterior occlusal areas with maximum interdigitation can be desired for proper positioning of the lower jaw to the upper jaw in the mouth of a patient. An unbalanced occlusion, such as a malocclusion, can be disruptive to the proper biting and chewing functions because excessive forces may be placed in a particular area that can lead to premature wear and/or restoration failure, or because undesirable forces such as flexion may lead to stresses which can cause abfraction lesions and/or crowding/spacing of the teeth. Accordingly, the position of a patient's jaw can be changed, for instance, using an orthodontic appliance (e.g., a dental appliance) to reduce or avoid such issues.

Current approaches for jaw repositioning, such as those performed prior to fixed orthodontic treatment (i.e., "braces") include having a treatment professional place an orthodontic appliance (which may include block elements, wires, tensioning springs, horizontal stops, etc.), which is firmly fixed to the teeth and which applies repositioning forces to move the jaw of the patient, thereby causing the relative positioning of the patient's upper and lower jaws to adjust. Some believe that this repositioning stimulates jaw growth in patients with growth potential remaining, while others believe that the muscles can re-learn a new position so long as the teeth are made to fit together well in the new jaw position.

As discussed above, current appliances for jaw repositioning are not designed to reposition the teeth during the process of jaw repositioning. As such, after adjustment of the position of the patient's jaw, further orthodontic treatment is performed to move and re-orient the teeth of the patient for improved dental interdigitation, if necessary.

Many of the current jaw repositioning devices can be displeasing to patients, both physically and aesthetically, because the patient does not have the option to remove the appliance even for a short period of time. Such appliances (e.g., a Herbst appliance) are typically cemented into place on the patient's teeth.

One factor to be weighed in adjusting the position of the mandible is the best fit or seating of the condyles of the mandible within the joint housing of the temporal bone. The position that is the most posterior-superior position of the condyle in the joint is usually an ideal position representing full seating. Another factor is the best fit of the teeth between the maxilla and the mandible.

Ideally, the teeth fit together best in occlusion with the left and right jaw joints fully seated at the same time, but this is not a requirement. Sometimes, the teeth fit together best with the condyles slightly displaced from the joint. As a result, when the condyles are fully seated, the teeth may not be in their best fitting position, in such instances. This condition is known as a shift between the centric relationship (condyles fully seated) and the centric occlusion (teeth best fitting).

Because the condylar relationship affords some flexibility in the positioning of the jaw, the lower jaw can be intentionally repositioned in accordance with the best fit of the teeth, for instance, by using an orthodontic appliance. The orthodontic appliances of the present disclosure that can be used may be more pleasing, both physically and aesthetically, to a patient undergoing treatment which intentionally repositions the lower jaw than appliances currently being utilized.

Depending on whether the jaw change is due to growth or muscular repositioning, realigning the teeth of a patient after repositioning the jaw can result in reversion of the position of the jaw if the teeth are not positioned and/or repositioned in a manner that best supports the new jaw position. This could occur, for example, if the teeth fit better in a jaw position different from the one which is accomplished through the jaw repositioning phase of the treatment.

In this situation, the jaw can revert toward its original position or whatever position is most comfortable for the patient when biting since the jaw repositioning appliance has been removed. Therefore, the desire is to reposition the jaw to an optimal relation while at the same time arrange the teeth such that they fit together in the best possible arrangement for the specific patient (as each patient's mouth has different characteristics and, therefore, each patient will have a different best outcome), both in arch coordination between the upper and lower arches and in interdigitation between the arches. The interdigitation makes the patient more likely to keep the lower jaw in the new position since the teeth fit together the better in the interdigitated position than in the non-interdigitated position.

Repositioning a jaw (e.g., separation of occlusal surfaces and/or moving the position of a lower jaw forward, backward, or laterally) according to embodiments of the present disclosure can include utilizing a set of one or more appliances, such as positioners, retainers, and/or other removable appliances (e.g., shells that don't reposition teeth and/or aligners) that are created, for example, by a treatment plan based on a virtual model of one or more jaws of a patient. In such embodiments, the treatment plan can include the use of a dental appliance having a first surface (inner surface) that defines a plurality of cavities shaped to receive a plurality of teeth, modify the virtual model of the jaw in a first configuration to include a virtual binding structure on a second surface (outer surface), the structure shaped to receive a specialized feature that provides one or more force characteristics, select a particular specialized feature as an attachment to the dental appliance, and adjust the virtual model of the jaw from a first configuration to a second configuration, based at least in part on a modeled force provided by the virtual binding structure and the particular specialized feature. In such a manner, each appliance can be modified to create a specialized device that can be used to correct specific features of issue for a patient.

For example, if an improperly positioned jaw is an issue, one or more repositioning jaw elements can place a force on the lower jaw of the patient to sagittally move the lower jaw. Movement of a jaw, as used herein, can include revising a position of a lower jaw relative to the upper jaw (e.g., in a forward, backward, and/or lateral direction). For instance, the position of the patient's lower jaw can shift to stimulate jaw growth in patients with growth potential remaining and/or to allow muscles to re-learn a new position. Such movement and other functions of the embodiments of the present disclosure are discussed in more detail below and some examples are shown in the accompanying drawings.

With respect to applications dealing with jaw repositioning, in various embodiments, the movement of the jaw can be controlled to reposition the patient's jaw in an anterior-posterior plane with respect to the jaws of the patient. For example, a first repositioning jaw element and a second repositioning jaw element can be positioned to interface as the patient moves to a fully engaged jaw position of the patient's upper dentition and the patient's lower dentition and wherein this movement is designed to reposition the patient's jaw in an anterior-posterior plane with respect to the jaws of the patient.

A dental appliance, in accordance with some embodiments of the present disclosure, can include a first shell having a number of tooth apertures configured to receive and reposition a number of teeth of a patient's upper dentition and/or a second shell having a number of tooth apertures configured to receive and reposition a number of teeth of the patient's lower dentition. Each shell (e.g., the first shell and second shell) can have one or more specialized features attached to a binding structure.

In some embodiments, the specialized features can be positioned on each respective shell to, for example, interact and/or interface at surfaces in the presence of a fully engaged jaw position of the patient's upper jaw and the patient's lower jaw in order to reposition the patient's jaw and/or separate occlusal surfaces of the patient's teeth for treatment purposes. A fully engaged jaw position, as used herein, can include a relationship of the mandible and the maxilla when the upper and lower jaw are closed as far as the dental appliance with the repositioning jaw elements will allow (e.g., a partial occlusal jaw position).

For example, the separation of occlusal surfaces of the patient's teeth can be used to treat sagittal malocclusions (including crossbites), deep bites, open bites, and/or other malocclusions, in various embodiments. The specialized features selected and positioned on the shell can be positioned such that the specialized features avoid interference with the shells of the dental appliance that are used to align the teeth.

For instance, the separation of occlusal surfaces can include the occlusal surfaces of at least some of the teeth within the shells and/or a portion of occlusal surfaces of the shells interacting with one or more surfaces of the specialized features of a shell on an opposing jaw. In this manner, a dental appliance in accordance with embodiments of the present disclosure can be used to concurrently treat sagittal malocclusions, including crossbite and/or deep bite, while simultaneously repositioning a number of teeth of the patient. Further, in some embodiments, all of this tooth and jaw movement can be planned via computing device executable instructions (e.g., as described with respect to FIG. 6) and therefore, excessive or redundant movements between the two typically separate processes can be avoided, among other benefits.

Additionally, a virtual model can be created and tested so that the patient does not have to be subjected to trial and error to achieve proper jaw and teeth positioning. The ability to visualize the repositioned jaws and establish the alignment in the repositioned configuration is advantageous because the best alignment of the teeth when the jaw is repositioned can be precisely established and can be different from the alignment when the jaws are not repositioned into an improved or optimal position.

In some embodiments, a plurality of appliances can be worn by a patient successively, for example, to achieve gradual simultaneous and/or sequential repositioning of the patient's jaw and/or gradual tooth movement. For instance, each of a plurality of dental appliances can reposition the patient's jaw in incremental distances. In such embodiments, the positions of the repositioning jaw elements can be adjusted to allow the treatment professional to fine tune the movement of the jaw symmetrically or asymmetrically and/or to move the teeth incrementally which may be less painful than with fixed appliances which may impart more sudden force in the initial period of the process than later in the process, among other benefits.

Figure 2:
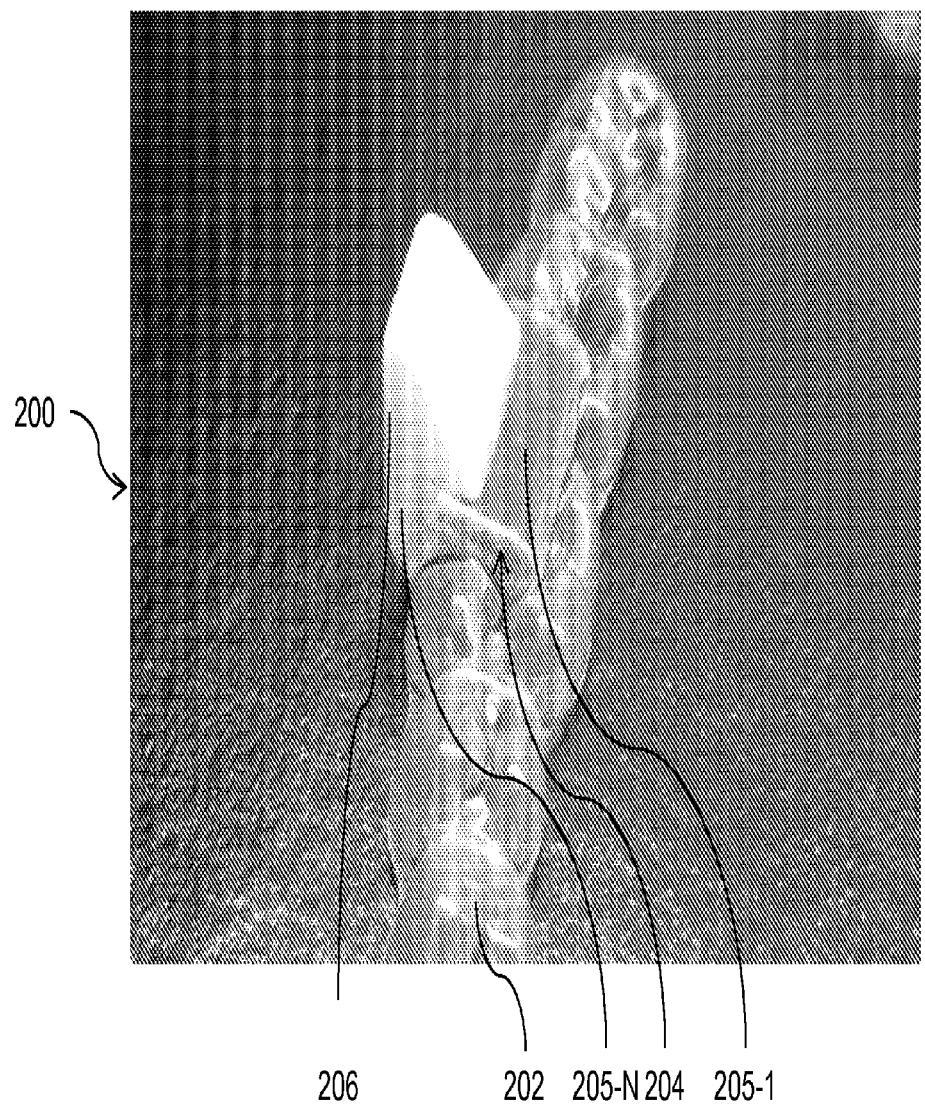
FIG. 2 illustrates a top view of a first shell with a binding structure thereon having a specialized feature attached thereto according to a number of embodiments of the present disclosure.

FIG. 2 illustrates a top view of a first shell with a binding structure thereon having a repositioning jaw element attached thereto according to a number of embodiments of the present disclosure. FIG. 2 provides an example of an embodiment of a dental appliance 200 that has a shell 202 with a number of cavities for receiving teeth, a binding structure 204, having multiple attachment surfaces 205-1 and 205-N, and a specialized feature 206 attached to the shell on at least one surface of the structure 204.

As in the embodiment of FIG. 1, in the example shown in FIG. 2, the binding structure 204 includes a first binding surface 205-1 (e.g., a planar platform) on the outer occlusal surface of the appliance and a second binding surface 205-N (e.g., a planar side surface) on the outer buccal surface of the appliance. In this manner, the specialized feature can be attached to one or more surfaces of the appliance (in the embodiment shown in FIG. 2, the specialized feature is attached to the first and second binding surfaces). As discussed above, attachment to multiple surfaces of the appliance can be beneficial, for example, to increase the amount of force that can be applied by the feature, provide forces in multiple directions, and other benefits.

Further, as discussed above, such attachment can be rigid, flexible, or a combination of rigid and flexible portions. For example, attachment to surface 205-1 may be rigid and attachment to surface 205-N may be flexible or attachment to a front portion of surface 205-1 may be rigid while attachment to a back portion of surface 205-1 may be flexible, in various embodiments, based on the type of attachment material used.

Figure 3:
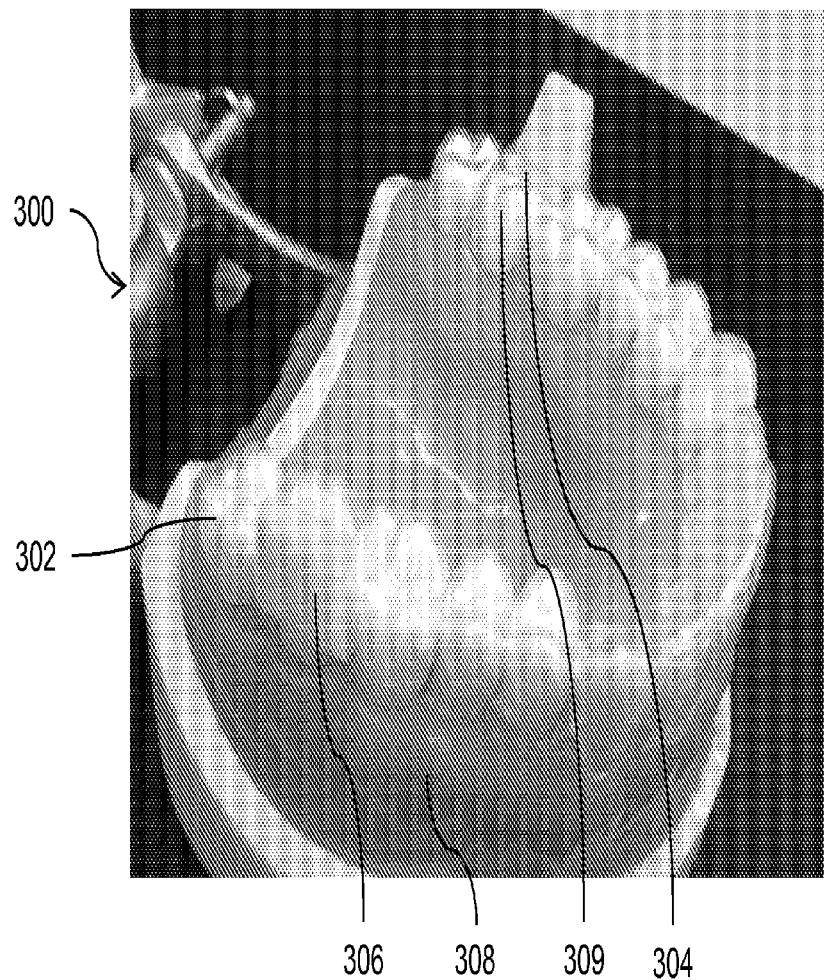
FIG. 3 illustrates an elevated side view of a shell with two binding structures thereon with each binding structure having a specialized feature attached thereto according to a number of embodiments of the present disclosure.

FIG. 3 illustrates an elevated side view of a shell with two binding structures thereon with each binding structure having a repositioning jaw element attached thereto according to a number of embodiments of the present disclosure. FIG. 3, shows a physical appliance 300 having a shell 302 positioned over a mold of the lower jaw of a patient's teeth 308 based on a particular stage in a treatment plan. As discussed herein, this could be one stage of multiple stages represented in physical form by a model.

In this embodiment, the binding surface 304 on the outer occlusal surface of the appliance only extends across a portion of the occlusal surface of the tooth 309. Such an embodiment may be beneficial in a situation in which the cavity surrounding the tooth 309 is used to provide force against one or more surfaces of the tooth and, therefore, a shape more conforming to the shape on the tooth can be utilized, among other benefits.

Figure 4:
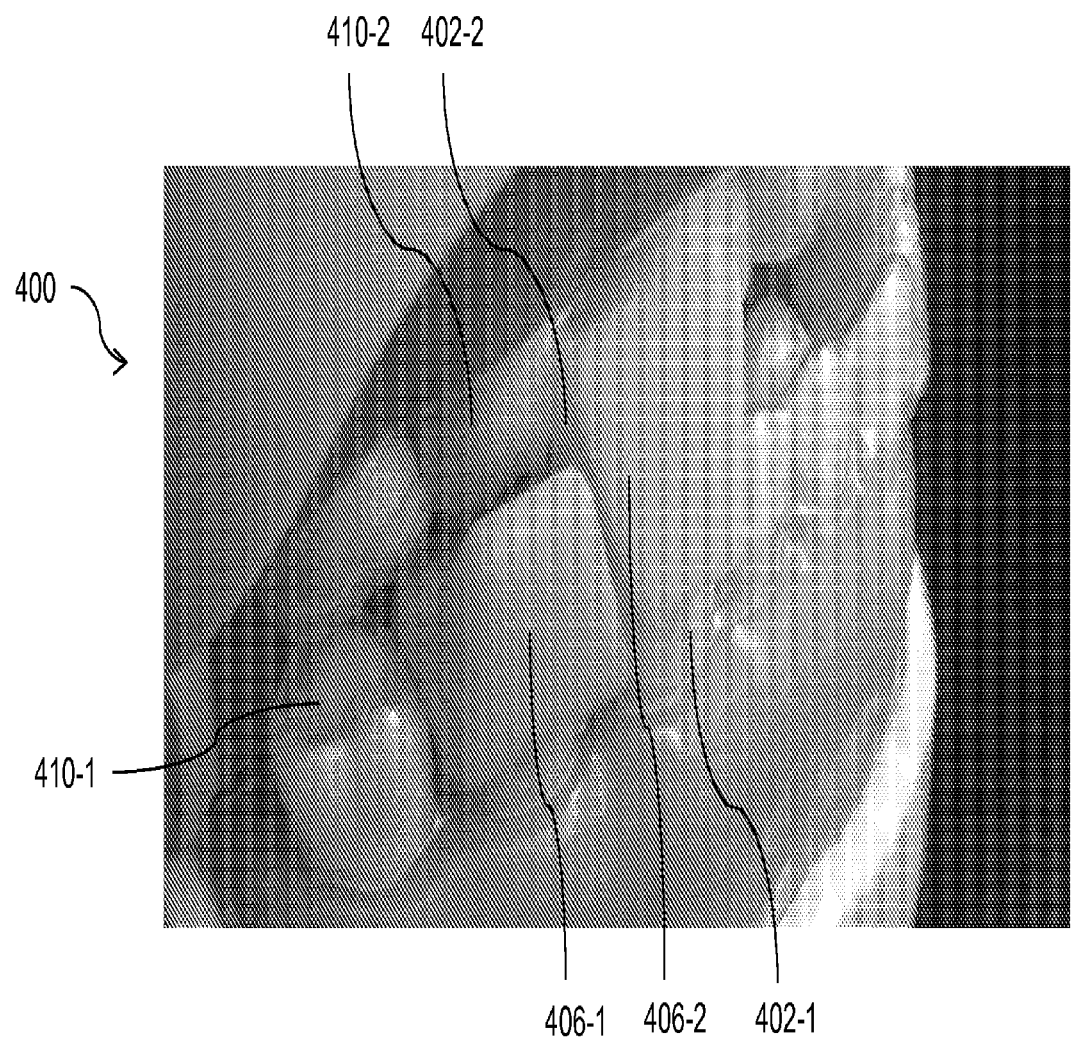
FIG. 4 illustrates a side view of an upper jaw having a first shell with a specialized feature attached to a binding structure thereon and a lower jaw having a second shell with a second specialized feature attached to a binding structure according to a number of embodiments of the present disclosure.

FIG. 4 illustrates a side view of an upper jaw having a first shell with a first repositioning jaw element attached to a binding structure thereon and a lower jaw having a second shell with a second repositioning jaw element attached to a binding structure according to a number of embodiments of the present disclosure. Such a configuration may be useful in repositioning a jaw of a patient.

For example, in some instances, the patient may exhibit abnormal occlusion or malocclusion. For instance, this may include a jaw (or both) that is protrusive, retrusive, or laterally displaced. As an example, positioning of the number of teeth of the patient's upper dentition and the number of teeth of the patient's lower dentition can be such that the best fit of the upper dentition with the lower dentition results in a misalignment of the lower jaw 410-1 relative to the upper jaw 410-2 either in positional relation or at the level of the jaw joint which connects the lower jaw to the upper jaw.

The lower jaw can be in a retruded position, for instance, resulting in a distance (e.g., space) between the front teeth of the upper dentition and the front teeth of the lower dentition (e.g., an increased overjet). Correction of the malocclusion can be beneficial to the patient in terms of improved chewing ability, reduced premature wear of the teeth, and/or improved facial aesthetics.

Although the specialized features and jaws illustrated in FIG. 4 are physical features and jaw models, similar virtual specialized features and virtual jaws of a patient can be presented on a computing device for purposes of treatment planning and/or in fabrication of such physical features and/or jaw models, in some embodiments. Examples of such virtual items include two dimensional or three dimensional versions of items devised via a treatment plan, devised by a treatment professional, and/or based on actual, physical items. An example of a system for providing such a virtual embodiment is described in more detail with respect to FIG. 6.

In the embodiment of FIG. 4, a specialized feature 406-1, as used herein, can extend beyond the occlusal plane of a shell 402-1 of a removable dental appliance 410-1 to engage with buccal or lingual coronal side surfaces of at least one tooth and/or a specialized feature 406-2 of shell 402-2 of a removable dental appliance 410-2 on the opposite jaw of the patient. The specialized features can, for instance, add retention to molar teeth to balance movement created by the repositioning jaw elements and/or prevent and/or limit a posterior surface of the removable dental appliance from contacting molars, among other functions. Through use of the specialized features shown in FIG. 4, the jaws of the patient can be aligned, both in an anterior-posterior relationship and in a lateral relationship (mesial-distal relationship).

In some embodiments, a removable dental appliance can, for example, include a first shell having a number of tooth apertures configured to receive a number of teeth of a patient's upper jaw, the first shell including a first binding structure positioned specific to the patient and having an attachment surface having a predetermined shape to mate with an attachment surface of a first specialized feature that can be attached to the first binding structure.

As discussed herein, the first and the second specialized features can be attached using an attachment material or via a mechanical locking mechanism having portions on both, the specialized feature and the binding structure that interlock to hold the binding structure and specialized feature together. For example, the appliance can include a shell having a number of tooth apertures configured to receive a number of teeth of a patient's lower jaw, the shell including a binding structure positioned specific to the patient such that a specialized feature can be attached to the binding structure, and wherein the binding structure includes a protruding element to mechanically lock with an intruding element of the specialized feature.

In some embodiments, one or more of the specialized features can be formed of a different material than a first shell, a second shell, and/or one or more of the binding structures. However, some embodiments can have the first shell, the second shell, and/or one or more of the binding structures formed of a same material (e.g., a polymeric material). Further, one or more of the specialized features can be formed of a same material as the first shell, the second shell, and one or more of the binding structures. This allows for additional customization of the appliance to the needs of the patient and may provide benefits in manufacturing the appliance.

The shapes and orientations of the binding structures can be varied as well. For example, the first binding structure and/or the second binding structure can extend from an occlusal surface of the first shell and the second shell, in some embodiments. The first binding structure and the second binding structure can also include surfaces that can be angled and protrude away from an occlusal plane of the patient (e.g., as illustrated in the embodiment of FIG. 1).

Some embodiments provide a dental appliance system having a number of components. For example, one system includes a first dental appliance including a first shell having a number of tooth apertures configured to receive a number of teeth of a patient according to a first stage of a treatment plan, the first shell including a first binding structure positioned specific to a tooth arrangement of the patient associated with the first stage such that a first specialized feature can be attached to the first binding structure.

The system also includes a second dental appliance including a second shell having a number of tooth apertures configured to receive a number of teeth of the patient according to a second stage of the treatment plan, the second shell including a second binding structure positioned specific to a tooth arrangement of the patient associated with the second stage such that a second specialized feature can be attached to the second binding structure. The first specialized feature can be attached to the first binding structure and the second specialized feature can be attached to the second binding structure.

In some such embodiments, the first dental appliance is configured to reposition a jaw of the patient a first incremental distance according to the first stage of the treatment plan. The first dental appliance can also be configured to reposition one or more teeth of the patient a first incremental distance according to the first stage of the treatment plan.

In various embodiments, the second dental appliance is configured to reposition the jaw of the patient a second incremental distance according to the second stage of the treatment plan. In this manner, the teeth can be moved in increments which can allow for providing more or less force to different teeth or portions of a jaw at different times during treatment. The first and second dental appliances can be part of a series of dental appliances and may not represent the first and second in the series, but rather may have appliances before the first appliance and have appliances after the second appliance.

Figure 5:
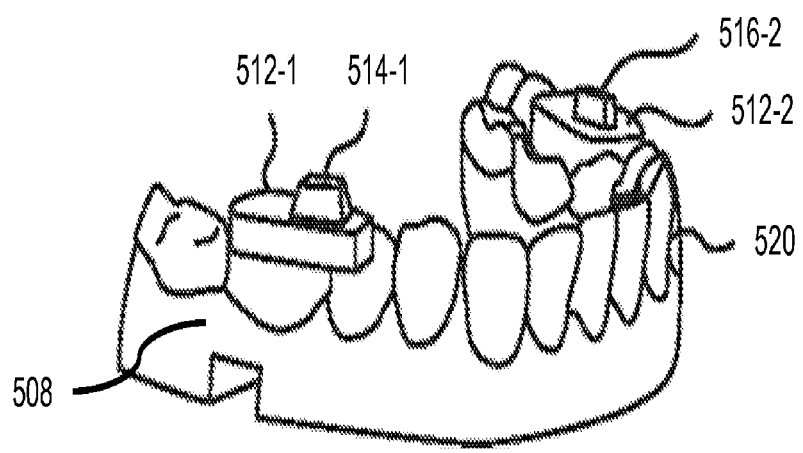
FIG. 5 illustrates an angled side view of a model for fabricating a shell with two binding structures thereon according to a number of embodiments of the present disclosure.

FIG. 5 illustrates an angled side view of a model for fabricating a shell with two binding structures thereon according to a number of embodiments of the present disclosure. In the embodiment of FIG. 5, a mold is illustrated which has a portion of a jaw of a patient 508 including a number of physical tooth models 520.

The mold also includes multiple binding structures 512-1 and 512-2. Each binding structure also includes a non-planar binding surface 514-1 and 514-2. In contrast to the planar binding surfaces of FIGS. 1-4, these binding surfaces include a portion that is non-planar and can provide a number of benefits, in some applications.

For example, when used with a mating surface on a specialized feature, the non-planar binding surface can provide added surface area to aid in attachment of the specialized feature and the binding surface. Further, in some embodiments (e.g., where the binding structure and the specialized feature are formed of different materials), the non-planar binding surface can provide a different characteristic to the specialized attachment.

Figure 6:
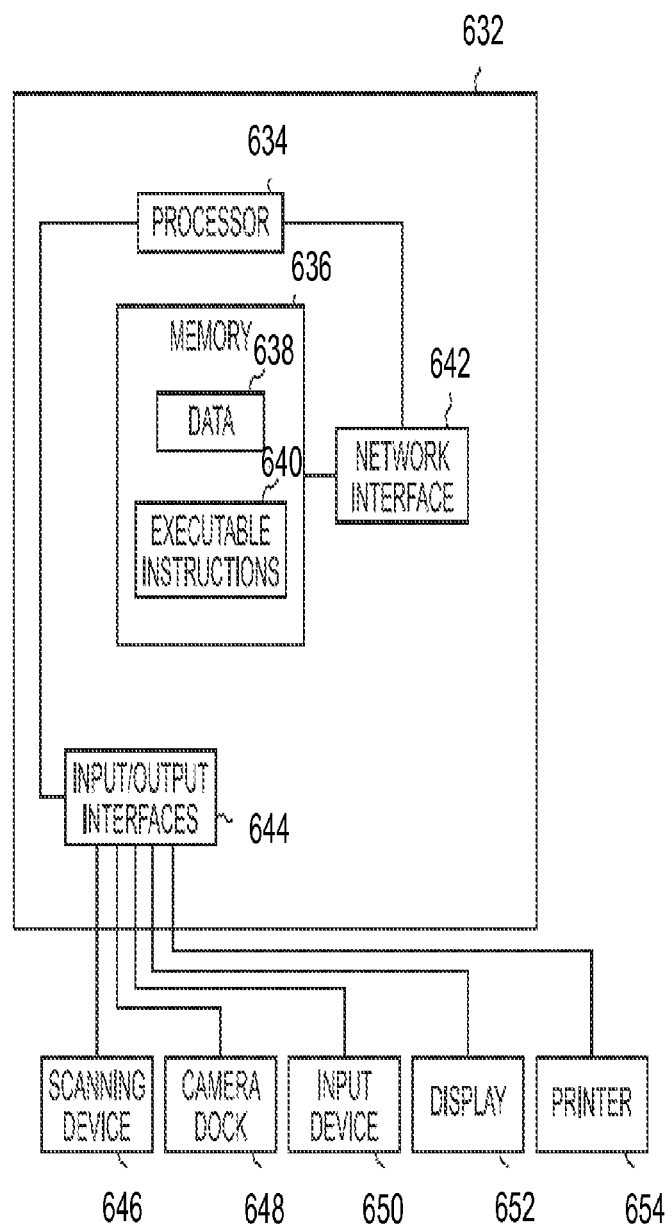
FIG. 6 illustrates a computing device that can be utilized according to one or more embodiments of the present disclosure.

For instance, the illustrated shape could provide increased rigidity to the interior of a specialized feature where the binding structure is of a more rigid material than the specialized feature. Some shapes may also reduce twisting force (e.g., the illustrated shape, having an elongate cross-ssection could be utilized to resist twisting). The characteristics of the interactions between the materials of the binding structure and the specialized feature as well as the shapes of the attachment surfaces of these items can be virtually modeled in some embodiments, for example, using a computing device system, as illustrated in FIG. 6, to determine a desirable combination to the used to treat a specific patient's one or more issues.

Through use of the treatment plan and/or virtual modeling, a dental appliance can be made, for example, by thermal-forming a sheet of plastic over a physical dental mold. The physical dental mold, for instance, can represent an incremental position to which a patient's teeth are to be moved.

The physical dental mold can be manufactured, for example, by downloading a computer-aided design (CAD) virtual dental model to a rapid prototyping process, such as, for example, a computer-aided manufacturing (CAM) milling, stereolithography, and/or photolithography process. In some implementations, the virtual dental mold can be hollowed out or "shelled" before sent for manufacturing to, for example, save on material cost, among other benefits.

The dental mold (e.g., set of molded teeth and/or jaw) can be created from a virtual model of a number of teeth and/or jaw of a patient. A virtual model, for example, can include an initial virtual dental model and/or intermediate virtual dental model (wherein the teeth of the patient have been moved with respect to their actual physical position). A dental mold can be formed in accordance with a unique treatment file that, for example, identifies a patient, a stage of a treatment plan, the virtual model of the number of teeth and/or jaw, and/or whether the dental mold is of the upper and/or lower dental arch.

In some computing device system embodiments, a treatment file can be accessed by a rapid prototyping apparatus machine, such as a SLA or 3D printing machine, to form and/or create the dental mold. As discussed above, the result of the dental mold can include a set of molded teeth.

The set of molded teeth can include at least a replica of the number of teeth of the patient. The dental mold can be used to make a dental appliance, for example, by creating a negative impression of the dental mold using polymeric sheets of material and vacuum forming the sheets over the dental mold, as discussed above.

For instance, a dental appliance can be formed by layering a thermoformable sheet of material and/or multiple sheets of one or more materials over the dental mold. The materials can include a polymeric material, for instance.

Generally, the dental appliance is produced and/or formed by heating the polymeric thermoformable sheet and vacuum or pressure forming the sheet over the dental mold (e.g., a number of molded teeth). The shape of the sheet of material can change thickness on some portions of the sheet as it conforms to the mold shape. A dental appliance can, for example, include a negative impression of the dental mold.

The appliance and/or parts thereof may be transparent, semi-transparent, or opaque in such a way as to emulate a natural tooth shade. However, embodiments in accordance with present disclosure are not so limited. For example, embodiments in accordance with the present disclosure can include forming a dental appliance utilizing a variety of techniques, such as SLA or 3D printing, among other techniques.

FIG. 6 illustrates a computing device that can be utilized according to one or more embodiments of the present disclosure. For instance, a computing device 632 can have a number of components coupled thereto. The computing device 632 can include a processor 634 and a memory 636. The memory 636 can have various types of information including data 638 and executable instructions 640, as discussed herein.

The processor 634 can execute instructions 640 that are stored on an internal or external non-transitory computer device readable medium (CRM). A non-transitory CRM, as used herein, can include volatile and/or non-volatile memory. Volatile memory can include memory that depends upon power to store information, such as various types of dynamic random access memory (DRAM), among others. Non-volatile memory can include memory that does not depend upon power to store information.

Memory 636 and/or the processor 634 may be located on the computing device 632 or off of the computing device 632, in some embodiments. As such, as illustrated in the embodiment of FIG. 6, the computing device 632 can include a network interface 642. Such an interface 642 can allow for processing on another networked computing device, can be used to obtain information about the patient, and/or can be used to obtain data and/or executable instructions for use with various embodiments provided herein.

As illustrated in the embodiment of FIG. 6, the computing device 632 can include one or more input and/or output interfaces 644. Such interfaces 644 can be used to connect the computing device 632 with one or more input and/or output devices 646, 648, 650, 652, 654.

For example, in the embodiment illustrated in FIG. 6, the input and/or output devices can include a scanning device 646, a camera dock 648, an input device 650 (e.g., a mouse, a keyboard, etc.), a display device 652 (e.g., a monitor), a printer 654, and/or one or more other input devices. The input/output interfaces 644 can receive executable instructions and/or data, storable in the data storage device (e.g., memory), representing a virtual dental model of a patient's dentition.

In some embodiments, the scanning device 646 can be configured to scan one or more physical dental molds of a patient's dentition. In one or more embodiments, the scanning device 646 can be configured to scan the patient's dentition and/or dental appliance directly. The scanning device 646 can be configured to input data into the computing device 632.

In some embodiments, the camera dock 648 can receive an input from an imaging device (e.g., a 2D or 3D imaging device) such as a digital camera, a printed photograph scanner, and/or other suitable imaging device. The input from the imaging device can, for example, be stored in memory 636.

The processor 634 can execute instructions to provide a visual indication of a treatment plan, a dental appliance, and/or a repositioning jaw element on the display 652. The computing device 632 can be configured to allow a treatment professional or other user to input treatment goals. Input received can be sent to the processor 634 as data 638 and/or can be stored in memory 636.

Such connectivity can allow for the input and/or output of data and/or instructions among other types of information. Some embodiments may be distributed among various computing devices within one or more networks, and such systems as illustrated in FIG. 6 can be beneficial in allowing for the capture, calculation, and/or analysis of information discussed herein.

The processor 634, in association with the data storage device (e.g., memory 636), can be associated with the data 638. The processor 634, in association with the memory 636, can store and/or utilize data 638 and/or execute instructions 640 for placing binding structures and/or virtual specialized features on a shell of a virtual model of a dental appliance. Such data can include the virtual dental model.

The virtual model of the dental appliance with the one or more binding structures and/or virtual specialized features can be used to create a physical dental appliance, for instance, as discussed further herein. The processor 634 coupled to the memory 636 can, for example, include instructions to cause the computing device 632 to perform a method including, for example, providing a virtual model of a dental appliance having a shell configured to reposition a number of teeth of a patient.

In some embodiments, the processor 634 coupled to the memory 636 can cause the computing device 632 to perform the method comprising identifying a misaligned jaw of a patient from a virtual image of the patient's jaw. The identification can include, for instance, determining a degree of the patient's jaw alignment utilizing the virtual image of the patient's jaw.

For example, identifying a misaligned jaw of the patient can include identifying a plurality of jaw placements of the virtual model of the jaw between stages of the treatment plan. Each of the plurality of jaw placements can be identified in a range of stages (e.g., can be associated with). A stage can include, for example, a predetermined period of time of the treatment plan (e.g., 2 weeks). A range of stages may be helpful (e.g., required) to reposition the jaws according to a treatment time used (e.g., needed) to re-posture the mandible.

For instance, a first jaw placement can be associated with a first range of stages (e.g., a first stage to a third stage) of the treatment plan and a second jaw placement can be associated with a second range of stages (e.g., a fourth stage to a fifth stage). A jaw placement, as used herein, can include a relation of the upper jaw and the lower jaw.

As an example, a 4 mm jaw reposition can be accomplished in a single jaw movement across twelve stages of a treatment plan (e.g., six months). Dental appliances associated with the twelve stages can include the same specialized features (e.g., repositioning jaw elements) designed to move the jaw toward the 4 mm corrected jaw position. However, as further discussed herein, the position and/or orientation of the repositioning jaw elements between stages can be adjusted based on differences in tooth positions and/or jaw relation of the patient.

By contrast, a 6 mm jaw reposition can be accomplished in two 3 mm jaw movements across sixteen stages of a treatment plan (e.g., eight months). Dental appliances associated with the first through eight stages of the sixteen stages can include a first set of repositioning jaw elements designed to move the jaw toward a 3 mm corrected jaw position. Dental appliances associated with the ninth through sixteenth stage of the sixteen stages can include a second set of repositioning jaw elements designed to move the jaw from the 3 mm corrected jaw position toward the 6 mm corrected jaw position (e.g., 3 mm additional jaw movement).

In some embodiments, the processor 634 coupled to the memory 636 can cause the computing device 632 to perform the method comprising providing a treatment plan for the patient. The treatment plan can include a virtual model of a dental appliance having a first shell and a second shell configured to reposition at least one tooth of the patient.

The at least one tooth can, for instance, include a tooth on a lower jaw and/or a tooth on an upper jaw of the patient. Further, the virtual model of the dental appliance can include repositioning jaw elements on the first shell and the second shell configured to move a position of the misaligned jaw of the patient (e.g., to move sagittally a position of the misaligned jaw of the patient).

In various embodiments, the processor 634 coupled to the memory 636 can cause the computing device 632 to perform the method comprising virtually testing the jaw movement to occur by the patient wearing the dental appliance. The virtual testing can include testing jaw movement, in addition to movement of teeth, in a number of embodiments.

The virtual binding structures and/or virtual specialized features can be adjusted based on the virtual testing of the jaw movement. For instance, the virtual binding structures and/or virtual specialized features can be adjusted to reach an intended jaw position and/or a final jaw position in a treatment plan. The virtual testing and/or adjustment, in some embodiments, can be across a number of stages of a treatment plan.

For example, for each stage of a treatment plan, the instructions can be executed to model forces applied to a virtual model of the jaw by an appliance corresponding to that stage (to simulate actual forces to be applied to a user's physical jaw by a physical appliance). Those forces can include forces applied to the virtual model of the jaw by the virtual binding structures and/or virtual specialized features, by virtue of the appliance being slightly out of alignment with a current configuration of the virtual model of the teeth and/or include forces applied to the aligner by the user (e.g., when the user wears the physical dental appliance).

Positioning and/or adjustment of positioning of virtual binding structures and/or virtual specialized features on a virtual model of a jaw can be automatic (e.g., by operation of software based on force modeling for a particular stage of treatment), manual (e.g., by operation of an operator interacting with the virtual model via an interface with a computing device), or a combination thereof. Likewise, the shape, size, orientation (e.g., various angles with respect to references), and/or attachment location (on the virtual teeth) of the virtual binding structures and/or virtual specialized features can be automatically set by the software, by manual operation (e.g., an operator can specify the necessary criteria of the virtual binding structures and/or virtual specialized features and/or modify default criteria provided by the software), or a combination thereof.

An automatic positioning of virtual binding structures and/or virtual specialized features on the virtual model of the jaw can, for example, occur in response to identifying the plurality of jaw placements of the virtual model of the jaw between stages of the treatment plan, as previously discussed. The position may be guided in part based on a posturing of the patient's jaw in a simulated advanced position, whereby the postured position is captured and/or an input by means of a bite registration that can be physical (e.g., wax or silicon bite) or digital (e.g., intraoral bite scan). Further, in some embodiments, the simulated advanced position may be based on photographs of the patient when the patient's jaw is in the advanced position. At least one of the plurality of jaw placements can be identified as a misaligned jaw, wherein the jaw placement is associated with a range of stages of the treatment plan.

A virtual model of a dental appliance having a first shell and a second shell can be provided for at least one stage of the range of stages with the identified misaligned jaw. Although embodiments are not so limited and embodiments in accordance with the present disclosure can include providing a treatment plan that includes virtual models of dental appliances (e.g., shells) for each stage of the treatment plan.

Virtual repositioning jaw elements can be positioned on the virtual teeth and/or virtual shells at the stage. For example, virtual binding structures and/or virtual specialized features can be positioned on shells of a first and a last stage of the range of stages with an identified misaligned jaw. The position at the first and the last stage of the range of stages can include an estimated initial binding structure and/or virtual specialized feature position and orientation.

The positioned binding structures and/or virtual specialized features can be refined at intermediate stages of the range of stages (e.g., between the first and the last stage of the range of stages). For example, the position at the first and the last stage of the range of stages can be interpolated with a refined position and orientation at the intermediate stages.

The positions at the first stage, last stage, and/or intermediate stages can be adjusted (to a refined position and orientation) to comply with a number of constraints, as discussed below. The refined position and orientation can include an optimized placement of the virtual binding structures and/or virtual specialized features.

That is, repositioning jaw elements for a first jaw placement that is associated with a number of stages can be the same virtual binding structures and/or virtual specialized features for each stage in the range of stages and/or can include incremental adjustments between stages. For example, the incremental adjustments can be based on differences in tooth positions and/or jaw position between stages.

Each repositioning jaw element within the range of stages can have a similar gross movement (e.g., move toward a corrected jaw position) with refined position and/or oriented (e.g., refined alignment with arch curve, refined angle of interface, etc.) based on the tooth placement and/or jaw position in the stage. The interpolation between stages can smooth the transition of the repositioning jaw elements between stages within the same range of stages.

As previously discussed, the dental appliances, in some embodiments, can reposition the teeth of the patient in parallel with jaw repositioning. In such embodiments, the stages of the treatment plan can be associated with tooth movement. For instance, movement of teeth of the patient across the stages of the treatment plan can be designed prior to, consecutively with, and/or subsequently to the jaw repositioning planning.

For example, movement of teeth of the patient toward a target position can be planned across a plurality of stages of the treatment plan. Prior to, consecutively with, and/or subsequently to planning the movement of teeth, the jaw repositioning can be planned. As previously discussed, a misaligned jaw of a patient associated with a range of stages of the treatment plan can be identified.

In some embodiments, during designing of the binding structures and/or specialized features, the movement of teeth can be revised based on and/or to allow for movement of the jaw. For example, the position of the patient's teeth can be revised to support the corrected jaw position and/or to allow for movement to the corrected jaw position. Thereby, the repositioning of the teeth can be planned in parallel with jaw repositioning planning.

As an example, the range of stages may be helpful because certain interferences between the upper jaw and the lower jaw may first be eliminated (e.g., such as movement of one or more teeth) before a more anterior position of the jaw of the patient is attained without significantly opening the bite.

The virtual dental appliance (e.g., virtual shells with the virtual binding structures and/or specialized features) can be designed using a number of constraints. A constraint, as used herein, can include a physical limit or restriction of the physical dental appliance to satisfy.

For example, the number of constraints can include physical limitations or restrictions of a placement and/or an orientation of the binding structures and/or specialized features in relation to a current tooth arrangement (e.g., surfaces of particular teeth, position of particular teeth, and/or the arch curve), a current jaw position, and/or a predicted corrected jaw position of the patient. A current tooth arrangement and/or current jaw position, as used herein, can include a tooth arrangement and/or jaw position of the patient at a particular stage of the treatment plan that the binding structures and/or specialized features are designed for.

The tooth arrangement and/or jaw position of the patient can, for example, change from one stage to another. Binding structures and/or specialized features can be positioned and/or oriented for a particular stage of a treatment plan based on the tooth arrangement and/or jaw position of the patient at the particular stage. The binding structures and/or specialized features can be the same for a range of stages of the treatment plan to accomplish a particular jaw movement. However, the position and/or orientation of the binding structures and/or specialized features can be adjusted (e.g., are different) between the stages of the range.

The constraints can be used to optimize placement of the virtual binding structures and/or specialized features. For instance, the constraints can each be satisfied, and/or satisfied to the greatest extent possible, to satisfy the greatest subset of the constraints.

For example, the virtual dental appliance can be designed by inputting a corrected jaw position of the patient and outputting binding structures and/or specialized features that can result in and/or move the jaw toward the corrected jaw position. A corrected jaw position can include a corrected relation of the upper jaw and the lower jaw as compared to the current jaw position of the patient, as previously discussed.

In some embodiments, the corrected jaw position can include an ideal jaw position. An ideal jaw position can include an optimal relation of the upper lower and lower jaw. The corrected jaw position can, for instance, be predicted (e.g., calculated) using patient data. For instance, the patient data can include articulation information and/or tooth data of the patient.

An occlusal plane, as used herein, is a direction that is determined based on the bite surface of a patient. As previously discussed, an occlusal plane is parallel to the bite surface of the teeth. An occlusal plane normal is perpendicular to the occlusal plane (e.g., bite surface) of the teeth of the patient, for example.

Figure 7:
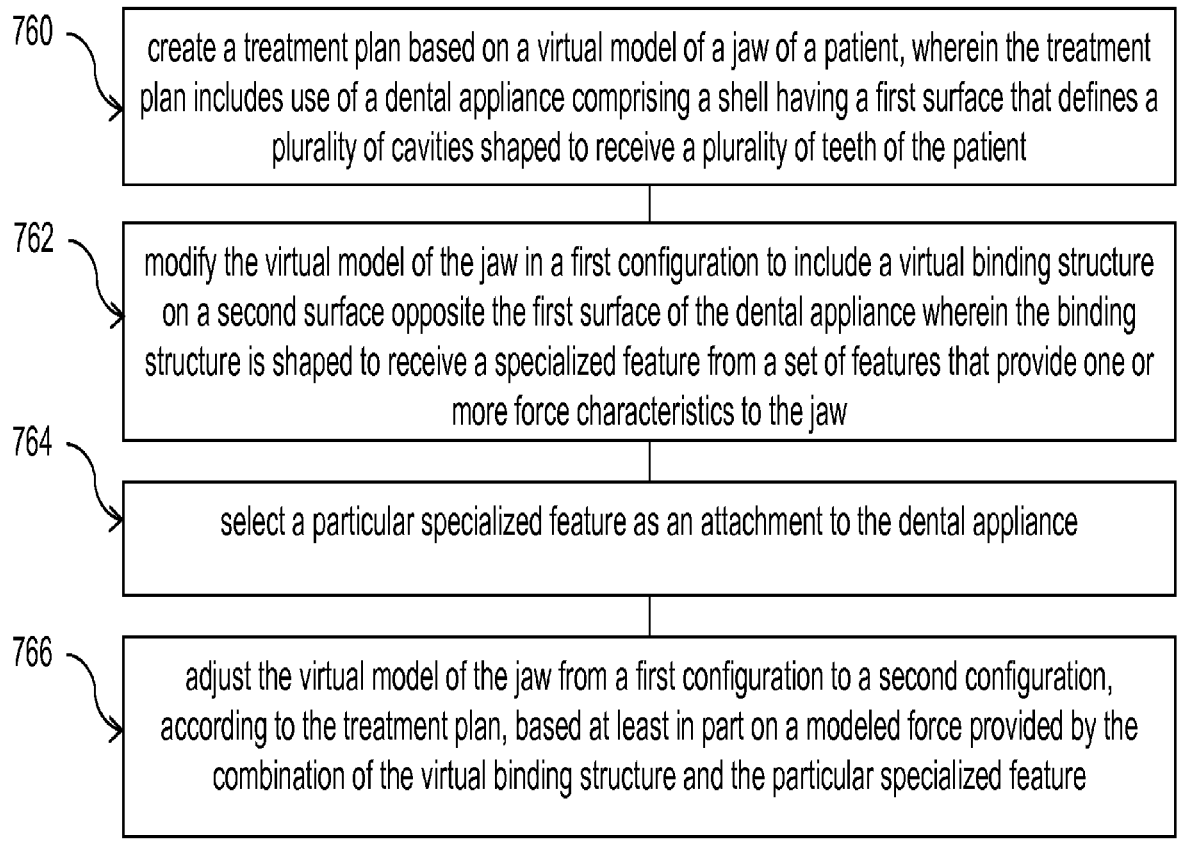
FIG. 7 illustrates a method according to one or more embodiments of the present disclosure.
Figure 8:
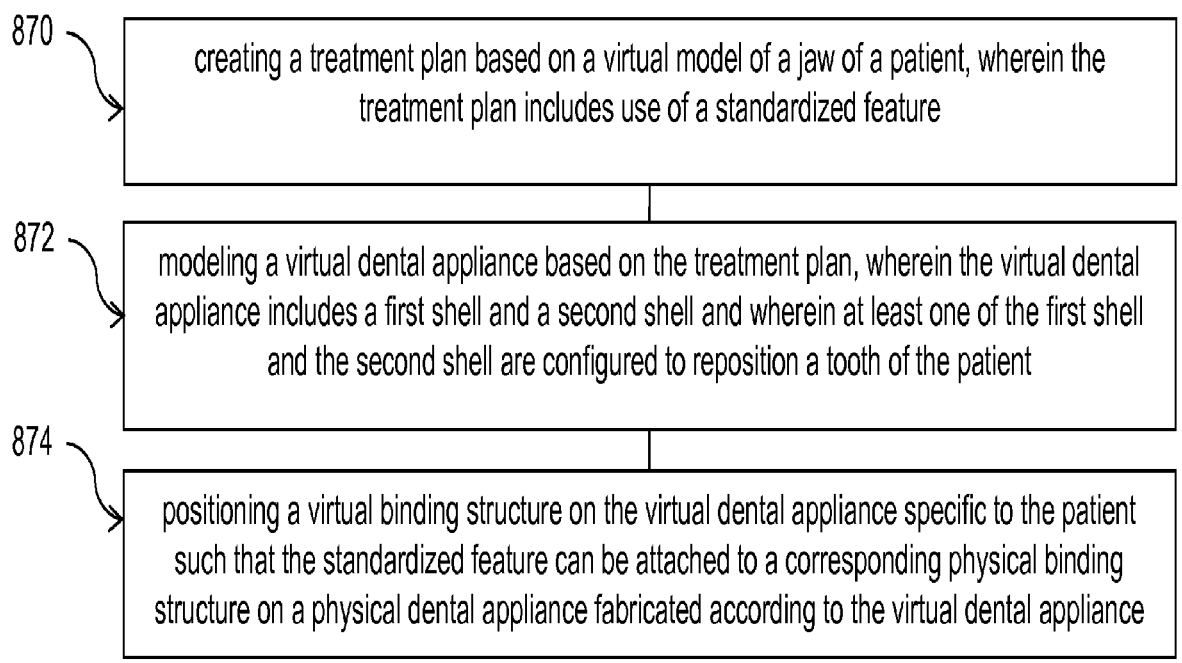
FIG. 8 illustrates a method according to one or more embodiments of the present disclosure.

A specific bite configuration, as used herein, can include one or more specific contacts between opposing teeth that are identified (e.g. a specific desired cusp-tip to fossa relationship or incisal edge to opposing fossae contact area). For instance, with a specific bite configuration the jaws are separated a specified amount in order to integrate the desired dental appliance features. In FIGS. 7 and 8, two examples of methods according to embodiments of the present disclosure are provided.

FIG. 7 illustrates a method according to one or more embodiments of the present disclosure. In such an embodiment, a processor (e.g., 634) coupled to memory (e.g., 636) can cause a computing device (e.g., 632) to create a treatment plan based on a virtual model of a jaw of a patient, wherein the treatment plan includes use of a dental appliance comprising a shell having a first surface that defines a plurality of cavities shaped to receive a plurality of teeth of the patient, at block 760.

The example instructions can also cause a computing device to modify the virtual model of the jaw in a first configuration to include a virtual binding structure on a second surface opposite the first surface of the dental appliance wherein the binding structure is shaped to receive a specialized feature from a set of features that provide one or more force characteristics to the jaw, at block 762, and select a particular specialized feature as an attachment to the dental appliance, at block 764. The virtual model of the jaw can then be adjusted from a first configuration to a second configuration, according to the treatment plan, based at least in part on a modeled force provided by the combination of the virtual binding structure and the particular specialized feature, as illustrated at block 766.

In some embodiments, a processor coupled to memory can cause a computing device to modify the virtual model of the jaw to include the virtual binding structure such that application of a force via a physical selected specialized feature to a physical binding structure of a dental appliance is formed based on the modified virtual model of the jaw which causes a movement of the patient's jaw according to the treatment plan. Embodiments can also include instructions to modify the virtual model of the jaw to include the virtual binding structure such that application of a force via a physical selected specialized feature to a physical binding structure of a physical dental appliance formed based on the modified virtual model of the jaw which causes a movement of at least one of the plurality of teeth of the patient according to the treatment plan. In this manner, the virtual model can model potential physical outcomes without having to create actual devices and test them on actual patients.

In various embodiments, the computing device can include instructions to modify the virtual model of the jaw in the second configuration to include a different virtual binding structure that is shaped to receive the selected specialized feature and further adjust the virtual model of the jaw from the second configuration to a third configuration, according to the treatment plan, based at least in part on a modeled force applied to the different virtual binding structure. In this manner, different binding structures can be tested virtually with different specialized features.

In some embodiments, the computing device can include instructions to modify the virtual model of the jaw in the second configuration to include a different specialized feature that is selected and that is shaped to be received on the virtual binding structure and further adjust the virtual model of the jaw from the second configuration to a third configuration, according to the treatment plan, based at least in part on a modeled force applied to the different selected specialized feature. Such embodiments can allow for force modeling with different specialized features to determine which feature may be the most appropriate feature to address a patient's one or more issues.

In various embodiments, creating a treatment plan can further include providing a virtual model of a plurality of virtual dental appliances, including the virtual dental appliance and wherein at least one of the other plurality of virtual dental appliances contains a different virtual binding structure or a different selected specialized feature. Accordingly, the treatment plan can utilize different specialized features during different stages of treatment. This can be accomplished on different appliances, or if the specialized features are removable, on the same appliance.

In some embodiments, the virtual image of the jaw of patient can include a virtual image of the mandible, its related soft and hard tissue, a number of teeth the patient's lower dentition, the maxilla, its related soft and hard tissues, and/or a number of teeth of the patient's lower dentition. The degree of the patient's jaw alignment can include, for instance, a path of articulation or jaw opening and closing. It may also include a repositioned location such as a protruded position, or a combination of semi-articulation and protrusion, for example.

Some embodiments can include providing a virtual model of a dental appliance having a shell configured to reposition a number of teeth of a patient. The virtual model of the dental appliance can, for instance, be created from a virtual model of the jaw of the patient and/or from a physical mold of the jaw of the patient. A virtual repositioning jaw element can, for example, be positioned on a binding structure of the shell of the virtual model of the dental appliance wherein an attachment surface of the binding structure can be parallel to a occlusal plane of the patient and when a repositioning jaw element is positioned thereon can include a portion that extends from a surface of the shell of the virtual model of the dental appliance.

In various embodiments, the computing device can include instructions to select an attachment type for attachment of the particular specialized feature to the dental appliance and adjust the virtual model of the jaw from a first configuration to a second configuration, according to the treatment plan, based at least in part on a modeled force provided by the combination of the virtual binding structure, the attachment type, and the particular specialized feature. In this manner, the selection of the attachment type can be tested to determine the most suitable attachment type for use with a specific patient.

FIG. 8 illustrates a method according to one or more embodiments of the present disclosure. In such an embodiment, a processor (e.g., 634) coupled to memory (e.g., 636) can cause a computing device (e.g., 632) to perform a method including, creating a treatment plan based on a virtual model of a jaw of a patient, wherein the treatment plan includes use of a specialized feature, at block 870. The method also includes modeling a virtual dental appliance based on the treatment plan, wherein the virtual dental appliance includes a first shell and a second shell and wherein at least one of the first shell and the second shell are configured to reposition a tooth of the patient, at block 872, and positioning a virtual binding structure on the virtual dental appliance specific to the patient such that the specialized feature can be attached to a corresponding physical binding structure on a physical dental appliance fabricated according to the virtual dental appliance, at block 874.

Such methods can also include wherein the virtual dental appliance is associated with a first stage of a plurality of stages of the treatment plan and creating the treatment plan includes providing virtual models of dental appliances for each stage of the treatment plan, wherein a position of the binding structure is adjusted for each stage of the treatment plan.

In some embodiments, the virtual binding structure includes a first virtual binding structure that extends from a surface of the first shell and wherein the virtual dental appliance includes a second virtual binding structure that extends from a surface of the second shell. In this manner, the treatment plan can include first and second shells each having a binding structure thereon and, as discussed herein, a same or different type of specialized feature and/or attachment material can be utilized to customize each of the shells to a particular patient's needs.

For example, in some embodiments, the method can include adjusting the position of the virtual binding structure to comply with a number of constraints, for example, wherein the number of constraints include aligning an interface of the specialized feature and another specialized feature with an occlusal plane normal of the patient. In various embodiments, the attachment of the specialized feature to the virtual binding structure can be displayed for viewing by the patient and/or treatment professional.

In some embodiments, creating the treatment plan can include identifying a misalignment in a jaw of the patient and selecting the specialized feature from a plurality of specialized features based on a treatment of the misaligned jaw. In this manner, a computing device via a processor can, for example, analyze data to identify whether a misalignment of a jaw is present in a patient and can select an appropriate specialized feature based on the analyzed data.

The positioning of the virtual repositioning jaw element and/or the design of the virtual specialized feature can be based on and/or included in a treatment plan. For instance, the treatment plan can include a desired, ideal, and/or final jaw positions and/or suggested positions for one or more specialized features (e.g., repositioning jaw elements) on a binding structure. The treatment professional can then review and revise these positions such that the virtual model of the dental appliance has a suggested or revised position of the specialized feature which can be used to create a physical dental appliance, for instance, as discussed further herein.

As discussed above, the virtual model of the dental appliance, including the virtual repositioning jaw element, can be used to determine a treatment plan for the patient and/or to form a physical dental appliance and/or physical repositioning jaw element (e.g., as discussed further herein).

In some embodiments, the virtual model can include the patient's upper jaw and/or lower jaw. A virtual model of one or more dental appliances (e.g., an appliance for the upper dentition and an appliance for the lower dentition which may also be connected together) each having a shell configured to reposition a number of teeth of the patient can be provided. The virtual model of the dental appliance can include a virtual model of a dental appliance configured to reposition the number of teeth of the patient.

Specialized features can be positioned on binding structures provided on occlusal, buccal, and/or lingual surfaces of a dental appliance to be placed over the patient's teeth. For instance, a virtual specialized feature can be positioned on the shell of the virtual model of the dental appliance parallel to an occlusal plane of the patient. An occlusal plane, as used herein, can include a surface from the incisal edges of the incisors and the tips of the occluding surfaces of the posterior teeth that is a mean of the curvature of the surface.

An appliance can, for example, be fabricated from a polymeric shell, and/or formed from other material, having a number of cavities shaped (e.g. tooth apertures) to receive and apply force to reposition one or more teeth from one geometric tooth arrangement to one or more successive tooth arrangements. There may be several appliances that may be needed to move the teeth from the beginning of a dental treatment plan to the end of the plan.

The shell may be designed to fit over a number of, or in many instances all, teeth present in the upper and/or lower jaw. For example, a shell can have a cavity that includes a number of tooth apertures for placement of teeth therein.

Each tooth aperture can include an interior surface (e.g., directly adjacent to the surfaces of the teeth placed therein) and an exterior surface. The interior surface is configured to receive and reposition a number of teeth of the patient, for example. In some situations, such as anterior crossbite and deep bite can be treated using the specialized features in the form of repositioning jaw elements to allow for individual movement of teeth while the jaws are repositioned into a new relative relationship.

Patients with crossbites and/or deep bites can have anterior incisors in the upper jaw and/or the lower jaw that are difficult to move into the desired location because teeth in the opposing jaw are a physical obstruction and therefore can prevent the desired movement from taking place, in some instances. The repositioning jaw elements (e.g., a twin block design wherein a first block is mounted to a binding structure of a upper shell (a first shell) and a second block is mounted to a binding structure of a lower shell (a second shell)) can provide separation of the upper jaw from the lower jaw (e.g., disclusion) by separating an occlusal surface of the first shell from an occlusal surface of the second shell.

The repositioning jaw elements can be positioned near posterior teeth, for instance, to allow for an anterior portion of the bite of the patient to open enough (e.g., disengage the occlusal interferences that may normally take place) to allow for easier treatment of the crossbite and/or deep bite. For instance, the separation of occlusal surfaces can be caused by preventing the cusp of the molars from sliding back into the fossae on the opposing molars. In such situations, the upper jaw and the lower jaw are held apart and avoid interfering with the prescribed treatment, for example.

The removable dental appliance can be configured to reposition a number of teeth of the patient's upper dentition and a number of teeth of the patient's lower dentition concurrently with repositioning of the patient's jaw. The simultaneous treatment of misalignment of a patient's jaw (e.g., Class II correction) in conjunction with teeth alignment issues (e.g., rotation, tipping, etc.) can shorten treatments times compared to sequential treatment protocols that first treat the misalignment of a patient's jaw before treating the misalignment of the patient's teeth. To help accomplish this objective, specialized features, in accordance with a number of embodiments, do not interfere with the engagement of the shell with the teeth contained therein.

The simultaneous treatment of misalignment of a patient's jaw concurrently with teeth misalignment can assist in the treatment of repositioning the patient's jaw. If untreated, teeth misalignment may encourage occlusion in the original jaw position instead of the desired jaw position (e.g., the intended or final jaw position), since the optimal interdigitation between the arches coincides with the original jaw position.

Realignment of the teeth so that the teeth fit together most desirable jaw position can reinforce the desired jaw position when the appliances are removed. Repositioning of the patient's jaw can include retraining the muscles associated with the movement of the lower jaw.

Due to the misalignment of a patient's teeth, a lower jaw of the patient can be incorrectly positioned in a retruded position because the teeth position with the best fit may force the jaw into a more retruded position than physiologically comfortable. A treatment whereby the teeth fit better in an anteriorly positioned mandible can relieve the joint compression that may take place when the mandible is retruded. The jaw muscles of the patient can be retrained to hold the lower jaw in a more forward (and more comfortable) position.

As discussed above, in some embodiments, a specialized feature can be hollow and/or can be filed with a material, such as a tooth colored material, a clear material, an acrylic, and/or a composite, among other materials, including materials that are printed via a three-dimensional (3D) printer or a through a stereolithography process. The extra material can, for instance, provide additional compressive strength as compared to a hollow specialized feature.

In various embodiments, the specialized feature can be made of a material that can be modified by the treatment professional (e.g. a material that can be filed down when appliance is fitted to the patient by a dentist, orthodontist, or dental hygienist or assistant, or a material to which the treatment professional can bond a shim or some other piece, if needed).

In some embodiments, the hollow space within the specialized feature can be used as a reservoir for the disbursement of medications or other items within the patient's mouth. For example, breath freshening agents, medications to aid in moving of teeth and/or improvement of the condition of the teeth and/or gums of the patient may be provided therein and dispensed through holes and/or passages formed in the interior and/or exterior sides of the specialized feature.

A hollow specialized feature can increase the flexibility of the shell to which the specialized feature is attached. The increased flexibility introduced can lower the functionality and/or the retention of the dental appliance in a vertical or horizontal direction. For example, as a patient moves to a fully engaged jaw position and the specialized features interface, the force placed on the shell can result in a gingival line of the shell flaring (e.g., moving away) from the gum line of the patient. In a number of embodiments, a number of design characteristics and/or elements can be used to reduce and/or eliminate the increase in flexibility, such as grooves and curved specialized features.

Additionally, in some embodiments, positioning the specialized features on the lingual surface of the shell can, for instance, result in a dental appliance that is more aesthetically pleasing to the patient because the specialized features are less visible to others (e.g., decreasing the prominence of the specialized features). Alternatively or in addition, a number of specialized features can extend from a lingual surface of the shells and a number of specialized features can extend from a buccal surface of the shell.

As discussed above, in some embodiments, the treatment plan can include multiple stages. As used herein, a "first stage" does not necessarily mean the original stage of a treatment plan, but is a relative term with respect to other stages. For example, the "first stage" may be a second stage of a 50 stage treatment plan, while the "second stage" may be a tenth stage of the 50 stage treatment plan, while the "third stage" may be a 30th stage of the 50 stage treatment plan, and the "fourth stage" may be a 46th stage of the 50 stage treatment plan.

The treatment plan may just treat the position of the jaw or, in some embodiments, the treatment of the position of the jaws can be combined with the movement of one or more teeth on one or both jaws. For instance, the series of dental appliances can be used to incrementally (e.g., in increments of 0.1 mm) move a position of a misaligned jaw of a patient. This can be beneficial as typical current jaw alignment techniques move a jaw in large increments, such as 0.5 mm or greater, which may cause discomfort to the patient, among other issues.

As discussed above, each treatment stage can include a gradual movement of a lower jaw of a patient. The increments can occur based on changes in the mesial-distal length of the repositioning jaw elements (i.e., specialized features and/or corresponding binding structures) and/or shifts in placement of the repositioning jaw elements on the shell (e.g. shift at least one repositioning jaw element in a mesial or distal direction).

Each dental appliance in the treatment plan (e.g., at each treatment stage) can be configured to reposition the number of teeth of the patient's upper dentition and the number of teeth of the patient's lower dentition and/or reposition of the patient's jaw. For instance, the repositioning of the patient's jaw can be incremental across the number of treatment stages.

An incremental reposition of the patient's jaw can include, for instance, gradual advancement of the lower jaw. As described herein, the gradual advancement can be achieved by shifting the placement of at least one of the repositioning jaw elements from a first stage (e.g., first dental appliance) to a second stage (e.g., second dental appliance) and/or changing the mesial-distal length of at least one of the repositioning jaw elements from a first stage to a second stage of the treatment plan.

The embodiments of the present disclosure provide for utilization of one or more binding structures on an appliance with one or more specialized features to provide specialized functionality to a patient based on their specific needs. Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description. The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method comprising:
   obtaining a treatment plan for a patient, the treatment plan providing first instructions to move a jaw of the patient from a first position toward a second position, and second instructions to move teeth of the patient from a first arrangement toward a second arrangement;
   placing a virtual binding structure on a particular location on a surface of a virtual model of the teeth;
   identifying a particular specialized feature as an attachment to include as part of a dental appliance at the particular location, the particular specialized feature providing one or more first force characteristics to implement the first instructions to move the jaw, and the dental appliance providing one or more second force characteristics to implement the second instructions to move the teeth;

selecting an attachment type for attachment of the particular specialized feature to the dental appliance;

adjusting the virtual model of the jaw from a first configuration to a second configuration, according to the treatment plan, based at least in part on a modeled force provided by the combination of the virtual binding structure, the attachment type, and the particular specialized feature; and displaying a virtual representation of the particular specialized feature at the particular location on the surface of the teeth.

2. The method of claim 1, further comprising:
modeling a movement of the jaw according to the treatment plan.

3. The method of claim 1, further comprising:
virtually testing movement of the teeth of the virtual model according to the treatment plan.

4. The method of claim 1, further comprising:
adjusting the virtual model of a jaw from a first configuration to a second configuration, according to the treatment plan, based at least in part on a first modeled force provided by a combination of the virtual binding structure and the virtual representation of the particular specialized feature;

modifying the virtual model of the jaw in the second configuration to include a different virtual binding structure that is shaped to receive the particular specialized feature; and further adjusting the virtual model of the jaw from the second configuration to a third configuration, according to the treatment plan, based at least in part on a second modeled force applied to the different virtual binding structure.

5. The method of claim 1, further comprising:
adjusting the virtual model of a jaw from a first configuration to a second configuration, according to the treatment plan, based at least in part on a first modeled force provided by a combination of the virtual binding structure and the virtual representation of the particular specialized feature;

modifying the virtual model of the jaw in the second configuration to include a different specialized feature that is selected and that is shaped to be received on the virtual binding structure; and further adjusting the virtual model of the jaw from the second configuration to a third configuration, according to the treatment plan, based at least in part on a second modeled force applied to the different selected specialized feature.

6. The method of claim 1, further comprising:
providing a virtual model of a plurality of virtual dental appliances to implement the treatment plan.

7. The method of claim 1, wherein the particular specialized feature comprises one or more repositioning jaw elements on one or more aligners used to implement the treatment plan.

8. The method of claim 1, wherein the particular specialized feature comprises one or more repositioning jaw elements on a plurality of aligners used to incrementally implement the second instructions.

9. The method of claim 1, wherein the particular specialized feature is part of twin blocks on one or more aligners used to implement the treatment plan.

10. The method of claim 1, wherein the particular specialized feature is configured to provide a separation between an upper jaw of the patient from a lower jaw of a patient to correct a Class II condition of the jaw.

11. The method of claim 1, wherein the particular location is on an occlusal surface of the virtual model of the teeth.

12. The method of claim 1, wherein the particular location is on a combination of a buccal surface and an occlusal surface of the virtual model of the teeth.

13. The method of claim 1, wherein the first force characteristics provide first corrections to a misalignment of the teeth and the second force characteristics provide second corrections to a Class II condition of the jaw.

14. The method of claim 1, wherein the attachment type includes a rigidity or flexibility of an attachment material, a mechanical property of an attachment structure, or whether an attachment allows the specialized feature to be removable from the dental appliance.

15. A system comprising:
one or more processors;
memory coupled the one or more processors, the memory storing instructions executable by the one or more processors to cause the system to:
obtain a treatment plan for a patient, the treatment plan providing first instructions to move a jaw of the patient from a first position toward a second position, and second instructions to move teeth of the patient from a first arrangement toward a second arrangement;

place a virtual binding structure on a particular location on a surface of a virtual model of the teeth;

identify a particular specialized feature to include as part of a dental appliance at the particular location, the particular specialized feature providing one or more first force characteristics to implement the first instructions to move the jaw, and the dental appliance providing one or more second force characteristics to implement the second instructions to move the teeth;

select an attachment type for attachment of the particular specialized feature to the dental appliance;

adjust the virtual model of the jaw from a first configuration to a second configuration, according to the treatment plan, based at least in part on a modeled force provided by the combination of the virtual binding structure, the attachment type, and the particular specialized feature; and display a virtual representation of the particular specialized feature at the particular location on the surface of the teeth.

16. The system of claim 15, wherein the particular specialized feature comprises one or more repositioning jaw elements on one or more aligners used to implement the treatment plan.

17. The system of claim 15, wherein the particular specialized feature comprises one or more repositioning jaw elements on a plurality of aligners used to incrementally implement the second instructions.

18. The system of claim 15, wherein the particular specialized feature is part of twin blocks on one or more aligners used to implement the treatment plan.

19. The system of claim 15, wherein the particular specialized feature is configured to provide a separation between an upper jaw of the patient from a lower jaw of a patient to correct a Class II condition of the jaw.

20. The system of claim 15, wherein the particular location is on an occlusal surface of the virtual model of the teeth.

21. The system of claim 15, wherein the particular location is on a combination of a buccal surface and an occlusal surface of the virtual model of the teeth.

22. The system of claim 15, wherein the first force characteristics provide first corrections to a misalignment of the teeth and the second force characteristics provide second corrections to a Class II condition of the jaw.

23. The system of claim 15, wherein the attachment type includes a rigidity or flexibility of an attachment material, a mechanical property of an attachment structure, or whether an attachment allows the specialized feature to be removable from the dental appliance.

24. A non-transitory computing device readable medium storing instructions executable by a processor to cause a computing device to:
obtain a treatment plan for a patient, the treatment plan providing first instructions to move a jaw of the patient from a first position toward a second position, and second instructions to move teeth of the patient from a first arrangement toward a second arrangement;
place a virtual binding structure on a particular location on a surface of a virtual model of the teeth;
identify a particular specialized feature to include as part of a dental appliance at the particular location, the particular specialized feature providing one or more first force characteristics to implement the first instructions to move the jaw, and the dental appliance providing one or more second force characteristics to implement the second instructions to move the teeth;
select an attachment type for attachment of the particular specialized feature to the dental appliance;
adjust the virtual model of the jaw from a first configuration to a second configuration, according to the treatment plan, based at least in part on a modeled force provided by the combination of the virtual binding structure, the attachment type, and the particular specialized feature; and
display a virtual representation of the particular specialized feature at the particular location on the surface of the teeth.

25. The non-transitory computing device readable medium of claim 24, wherein the attachment type includes a rigidity or flexibility of an attachment material, a mechanical property of an attachment structure, or whether an attachment allows the specialized feature to be removable from the dental appliance.

* * * * *